US012668671B2

(12) United States Patent
Knör

(10) Patent No.: US 12,668,671 B2
(45) Date of Patent: Jun. 30, 2026

(54) FINELY DIVIDED AQUEOUS PARTICLE-STABILIZED PICKERING EMULSION AND PARTICLES PRODUCED THEREFROM

(71) Applicant: WACKER CHEMIE AG, Munich (DE)

(72) Inventor: Sebastian Knör, Emmerting (DE)

(73) Assignee: Wacker Chemie AG, Munich (DE)

( * ) Notice: Subject to any disclaimer, the term of this patent is extended or adjusted under 35 U.S.C. 154(b) by 795 days.

(21) Appl. No.: 17/786,747

(22) PCT Filed: Dec. 17, 2019

(86) PCT No.: PCT/EP2019/085651
§ 371 (c)(1),
(2) Date: Jun. 17, 2022

(87) PCT Pub. No.: WO2021/121562
PCT Pub. Date: Jun. 24, 2021

(65) Prior Publication Data
US 2023/0064513 A1     Mar. 2, 2023

(51) Int. Cl.
| | |
|---|---|
| *C08J 3/12* | (2006.01) |
| *A61K 8/25* | (2006.01) |
| *A61K 8/891* | (2006.01) |
| *C08K 9/06* | (2006.01) |
| *C08L 83/04* | (2006.01) |
| *C09C 1/30* | (2006.01) |
| *C09C 3/12* | (2006.01) |
| *C09D 7/40* | (2018.01) |
| *C09D 7/65* | (2018.01) |
| *C09D 183/04* | (2006.01) |
| *C09K 23/54* | (2022.01) |

(52) U.S. Cl.
CPC .............. *C08J 3/128* (2013.01); *A61K 8/25* (2013.01); *A61K 8/891* (2013.01); *C08K 9/06* (2013.01); *C08L 83/04* (2013.01); *C09C 1/3081* (2013.01); *C09C 3/12* (2013.01); *C09D 7/65* (2018.01); *C09D 7/70* (2018.01); *C09D 183/04* (2013.01); *C09K 23/54* (2022.01); *A61K 2800/623* (2013.01); *A61K 2800/651* (2013.01); *C01P 2004/62* (2013.01); *C01P 2006/22* (2013.01); *C08J 2383/07* (2013.01);

*C08K 2201/005* (2013.01); *C08L 2201/52* (2013.01); *C08L 2207/324* (2013.01)

(58) Field of Classification Search
CPC ......... C08J 3/128; C08J 2383/07; C09D 7/65; C09D 7/70; C09D 183/04; C09K 23/54; A61K 8/25; A61K 8/891; A61K 2800/623; A61K 2800/651; C08K 9/06; C08K 2201/005; C08L 83/04; C08L 2201/52; C09C 1/3081; C01P 2004/62; C01P 2006/22

See application file for complete search history.

(56) References Cited

U.S. PATENT DOCUMENTS

| | | | | |
|---|---|---|---|---|
| 2009/0176920 A1* | 7/2009 | Sandmeyer | ................ | C08J 3/03 |
| | | | | 524/588 |
| 2017/0319458 A1 | 11/2017 | Matsufuji et al. | | |
| 2018/0325784 A1* | 11/2018 | Chari | ....................... | A61K 8/25 |
| 2019/0055365 A1* | 2/2019 | Morita | ................... | A61Q 17/04 |

FOREIGN PATENT DOCUMENTS

| | | |
|---|---|---|
| DE | 19742761 A1 | 4/1999 |
| DE | 10349082 A1 | 5/2005 |
| DE | 102006014875 A1 | 10/2007 |
| DE | 102015216415 A1 | 3/2017 |
| EP | 0433727 B1 | 8/1995 |
| EP | 1433749 B1 | 4/2006 |
| JP | 2019202236 A | 11/2019 |
| JP | 2019210203 A | 12/2019 |
| WO | 2007113095 A1 | 10/2007 |
| WO | 2017142068 A1 | 8/2017 |

OTHER PUBLICATIONS

Swinscow, Statistics at Square One, Chapter 2: Mean and Standard Deviation, 1997, BMJ Publishing Group. (Year: 1997).*
CDC, Niosh Pocket Guide to Chemical Hazards, Silica, amorphous, 2019. (Year: 2019).*
Teixeira et al, Pickering Emulsion Polymerization Using Laponite Clay as Stabilizer to Prepare Armored "Soft" Polymer Latexes, 2011, Macromolecules, 44, p. 7415-7422. (Year: 2011).*
Research progress on the stability of Pickering emulsion, Yang Chuanxi et al., Science and Technology Introduction, Feb. 29, 2018.

* cited by examiner

*Primary Examiner* — Mark Eashoo
*Assistant Examiner* — Caitlin Norine Illing

(57) ABSTRACT
An aqueous, particle-stabilized Pickering emulsion along with methods or processes for producing the same and particles produced therefrom.

10 Claims, No Drawings

FINELY DIVIDED AQUEOUS PARTICLE-STABILIZED PICKERING EMULSION AND PARTICLES PRODUCED THEREFROM

CROSS-REFERENCE TO RELATED APPLICATIONS

This application is a U.S. National Phase application of PCT Application No. PCT/EP2019/085651 filed on Dec. 17, 2019 the disclosure of which is incorporated by reference herein in its entirety.

The invention relates to an aqueous, particle-stabilized Pickering emulsion of a material amenable to polyaddition, to polycondensation or to chain polymerization, to a process for producing said emulsion, to a process for producing particles from this Pickering emulsion, and to particles.

WO2017142068A1 discloses finely divided, silica-stabilized emulsions of reactive, addition-crosslinking siloxanes, a disadvantage being the use of very large amounts of silica. The core of the silicone elastomer particles is formed by way of a polyaddition reaction.

WO2007113095 as well describes the production of silicone particles by way of silica-stabilized emulsions. It is taught that the size of the particles can be controlled for example by the emulsifying technique, in other words, for instance, by variables such as the shearing energy introduced, the volume fraction of the disperse silicon-organic phase, the amount of the stabilizing, finely divided metal oxide particles, the pH of the continuous water phase and its ionic strength, the viscosity, the sequence of the metering, and the metering rate, or by the reaction regime, in other words, for example, by the reaction temperature, the reaction time, and the concentration of the raw materials used. The selection and the amount of the hydrolysis and condensation catalyst optionally employed likewise influence the particle size.

WO2007113095 additionally teaches that when using an emulsifying technique which allows the production of relatively small droplets, this process results in small, surface-structured particles. For this purpose it is possible for example to use different shearing energies or a selection of different amphiphilic particles in order to stabilize the condensable liquid or preparation in water.

A subject of the present invention is a process for producing an aqueous, particle-stabilized Pickering emulsion (E) of a material (S) amenable to polyaddition, to polycondensation or to chain polymerization and selected from siloxane and silane, by mixing an aqueous phase (W), a material (S) amenable to polyaddition, to polycondensation or to chain polymerization and selected from siloxane and silane, and a particulate solid (F), forming droplets having a mean diameter $d_{50}$ of at most 9 μm and comprising the material (S) and the particulate solid (F), with the proviso that in the particle-stabilized Pickering emulsion the mass ratio $Q1=m(F)/m(S)*100$ is any number from 3 to 25, the mass ratio $Q2=m(S)/(m(S)+m(W))*100$ is any number from 50 to 75, and the relationship between Q1 and Q2 is $Q2=-(1.56*Q1)+Q3$, where Q3 is a number between 77.0 and 89.0.

Surprisingly it has been found that the finely divided, aqueous, particle-stabilized Pickering emulsions (E) are formed when the mass ratios described above are observed. Finely divided emulsions (E) of this kind are otherwise accessible only using organic emulsifiers, which cause disruption by adhering to the droplets.

The size of the droplets, with a mean diameter $d_{50}$ of less than 9 μm, in the process of the invention is largely independent of the mixing process and the mixing energy. This makes the process of the invention substantially more robust and allows a change in the batch size or in the mixing process, such as on operational scale-up, for example, without the need for costly and inconvenient adaptation of the formula or of the process.

Relative to the non-invention-compliant, coarsely particulate emulsions of the prior art, the Pickering emulsions (E) have the advantage that they exhibit improved stability toward separation, meaning that they are largely stable toward creaming or sedimentation of the disperse phase.

The Pickering emulsion E preferably exhibits no significant separation within 21 days of storage at room temperature.

A further advantage of the Pickering emulsions (E) is that they have low shear viscosities and hence enable easy application. The aqueous emulsions of the invention have the advantage, furthermore, that in a closed system at room temperature they have a high storage stability of at least 15 months.

An additional advantage of the Pickering emulsions (E) is that there is no need at all for organic emulsifiers and hence, among other benefits, the water resistance of the contact faces between the resultant shaped articles and the substrates, and the adhesion to the substrates, are greatly improved. As a result of the omission of organic emulsifiers, the particles P producible from the Pickering emulsions (E) are free from organic emulsifiers. This is a great advantage for cosmetic applications, where such contaminants reduce the product quality or indeed are undesirable.

The process of the invention for producing the Pickering emulsions (E) affords the advantage that finely divided emulsions can be generated, without the need to use a very large excess of stabilizing particles. As a result, unreactive contaminants which may enter the environment, and which adversely affect the activity of the crosslinkable emulsions, are avoided in the Pickering emulsions (E).

The Pickering emulsions (E) have the advantage that, in contrast to existing systems, their rheology can be adjusted in ranges of the kind known for the nonaqueous systems.

A further advantage of the Pickering emulsions (E) is that the mechanical properties of the fully cured products are situated within ranges of the kind known for the nonaqueous systems.

The Pickering emulsions (E) have the advantage, additionally, that they can be formulated such that no volatile organic compounds at all are emitted to the atmosphere in the course of curing.

The Pickering emulsions (E) have the advantage, additionally, that they form firmly adhering coatings on numerous substrates, such as, for example, paper, fabrics, mineral building materials, such as fiber cement, plastics, wood, and many other substrates. As a result they are also suitable for adhesively bonding many substrates. Coating here may be accomplished, for example, by brushing, rolling, dipping or spraying.

The Pickering emulsions (E) of crosslinkable organopolysiloxanes have the advantage over the non-invention-compliant, coarsely particulate emulsions that the reactive organopolysiloxane, in coating, impregnating and hydrophobizing processes, because of the smaller droplet size, is able to penetrate more deeply into the substance to be treated, thereby improving the activity and durability of the surface treatment. A very high excess of particulate emulsifier, as used in the prior art, would clog the pores of the substance to be treated and would deposit on the surface. This reduces the activity of the application. The process of the invention for producing the Pickering emulsions (E) enables the production of finely divided emulsions without the use of a large excess of particulate emulsifier. If using organic emulsifiers of the kind used in the prior art, they would deposit on the surface. This results in unwanted effects—for example, organic emulsifiers impair the printability of the surfaces and the adhesion on bonding.

Another subject of the present invention is the aqueous, particle-stabilized Pickering emulsion (E) producible by the process above.

The droplets which comprise the material (S) and the particulate solid (F) form the discontinuous phase of the Pickering emulsion (E).

The discontinuous phase comprises preferably material amenable to polyaddition, to polycondensation or to chain polymerization and comprising at least one or more siloxanes or silanes.

Preferably the material (S) is at least one siloxane amenable to polyaddition, to polycondensation or to chain polymerization and of the general formula (IV)

$$[A^1{}_m R^9{}_p SiO_{(4-p-m)/2}] \quad (IV),$$

where

A$^1$ is a hydrogen or hydrocarbon radical which contains up to 30 carbon atoms and may additionally contain heteroatoms selected from O, S, Si, Cl, F, Br, P or N atoms, and so A$^1$ may also be a functional group, which itself is unsubstituted or substituted, R$^9$ denotes alkoxy or aryloxy radicals having up to 18 carbon atoms, or hydroxyl radicals or H, or which independently of A$^1$ may have the definition thereof, m and p each denote the values 0, 1, 2 or 3, or at least one silane amenable to polyaddition, to polycondensation or to chain polymerization and of the general formula (V), $$(R^{10})_{4-n}\text{-Si}\text{—}(OR^{11})_o \quad (V),$$

where o is a number with a value of 1, 2, 3 or 4,

R$^{10}$ denotes linear or branched alkyl radicals having 1 to 16 carbon atoms, where nonadjacent carbon atoms may be replaced by oxygen atoms, or denotes aryl radicals or is an organofunctional radical selected from the group of phosphonic monoester radical, phosphonic diester radical, phosphonic acid radical, methacryloyloxy radical, acryloyloxy radical, vinyl radical, mercapto radical, isocyanato radical, where the isocyanato radical may optionally be reaction-blocked for protection from chemical reactions, hydroxyl radical, hydroxyalkyl radical, vinyl radical, epoxy radical, glycidyloxy radical, morpholino radical, piperazino radical, a primary, secondary or tertiary amino radical having one or more nitrogen atoms, where the nitrogen atoms may be substituted by hydrogen or by monovalent aromatic, aliphatic or cycloaliphatic hydrocarbon radicals, carboxylic acid radical, carboxylate anhydride radical, aldehyde radical, urethane radical, urea radical, where the radical R$^{10}$ may be bonded directly on the silicon atom or may be separated therefrom by a carbon chain of 1-6 carbon atoms, and R$^{11}$ is a monovalent, linear or branched aliphatic or cycloaliphatic hydrocarbon radical in which nonadjacent carbon atoms may be replaced by heteroatoms such as O, N, P, S, Cl, F, Br or Si, where the free valences of the relevant heteroatoms may be saturated by linear or branched alkyl radicals or by hydrogen atoms, or is a monovalent, aromatic hydrocarbon radical or a radical of the form —C(=O)—R$^{12}$, where R$^{12}$ is a monovalent, linear or branched aliphatic or a cycloaliphatic hydrocarbon radical or a monovalent, aromatic hydrocarbon radical, where the selected silane or optionally the selected silanes may be present in nonhydrolyzed form, in hydrolyzed form, or in hydrolyzed and partly condensed or hydrolyzed and condensed form, or in a mixture of these forms, or a preparation of two or more such siloxanes of the general formula (IV) and/or silanes of the general formula (V).

The silane, siloxane or preparation is preferably one amenable to polycondensation or to polyaddition, with particular preference being given to a silane, siloxane or preparation which is amenable to polyaddition.

The silane, siloxane or preparation which is amenable to polyaddition, to polycondensation or to chain polymerization is preferably liquid at room temperature and under the pressure of the surrounding atmosphere, in other words 1013 hPa, and preferably has a viscosity of 1 to 500 000 mm$^2$/s, more preferably of 10 to 100 000 mm$^2$/s, very preferably 50 to 50 000 mm$^2$/s, especially preferably of 100 to 10 000 mm$^2$/s.

In one preferred embodiment a preparation is used which is composed of at least one vinyl group-containing organopolysiloxane and of at least one organopolysiloxane having silicon-bonded hydrogen atoms, the preparation having a viscosity of 150 mm$^2$/s to 8000 mm$^2$/s at 25° C.

In one especially preferred embodiment a preparation is used which is composed of at least one vinyl group-containing organopolysiloxane, of at least one vinyl group-containing organopolysiloxane resin and of at least one organopolysiloxane having silicon-bonded hydrogen atoms, the preparation having a viscosity of 500 mm$^2$/s to 5000 mm$^2$/s at 25° C.

The material (S) preferably comprises one or more siloxanes composed of repeating units of the general formula (IV) and/or silanes of the general formula (V).

Although not indicated in the general formula (IV), up to 10 mol percent of the diorganosiloxane units may be replaced by other siloxane units, which, however, are usually present only in the form of more or less hard-to-avoid impurities, such as $R_3SiO_{1/2}$, $RSiO_{3/2}$ and $SiO_{4/2}$ units, where R has the definition indicated above for A$^1$.

The particulate solid (F) used in the invention preferably comprises particles which are solid at room temperature and under the pressure of the surrounding atmosphere, in other words 1013 hPa.

The particulate solid (F) preferably has a solubility in water at pH 7.33 and an electrolyte background of 0.11 mol and a temperature of 37° C. of less than 0.1 g/l, more preferably of less than 0.05 g/l, under the pressure of the surrounding atmosphere, in other words 1013 hPa.

The particulate solid (F) preferably has a molar mass of greater than 10 000 g/mol, more preferably a molar mass of 50 000 to 50 000 000 g/mol, more particularly of 100 000 to 10 000 000 g/mol, measured in each case preferably by means of static light scattering.

The particulate solid (F) preferably has a specific BET surface area of 30 to 500 m$^2$/g, more preferably of 100 to 300 m$^2$/g. The BET surface area is measured by known methods, preferably in accordance with German Industrial Standard DIN 66131 and DIN 66132.

The particulate solid (F) preferably has a Mohs' hardness of greater than 1, more preferably greater than 4.

The particulate solid (F) used is preferably a metal oxide having a covalent bonding component in the metal-oxygen bonding, examples being solid oxides of the main and transition group elements, such as of the $3^{rd}$ main group, such as boron, aluminum, gallium and indium oxides, of the $4^{th}$ main group, such as silicon dioxide, germanium dioxide, and tin oxide and dioxide, lead oxide and dioxide, or an oxide of the transition group elements, such as titanium dioxide, zirconium dioxide, hafnium dioxide, cerium oxide or iron oxide.

The metal oxides used in the invention are preferably aluminum(III) oxides, titanium(IV) oxides, and silicon(IV) oxides, such as wet-chemically produced—for example, precipitated—silicas or silica gels, or aluminum oxides, titanium dioxides or silicon dioxides which are produced in operations at elevated temperature, such as, for example, pyrogenically produced aluminum oxides, titanium dioxides or silicas, with pyrogenic silica being particularly preferred.

The pyrogenic silicas are preferably silanized pyrogenic silicas having a methanol number of less than 70.

Very particular preference is given to partially water-wettable metal oxides as described in EP 1433749 A1 and DE 10349082 A1.

The mean particle size of the particulate solid (F) or, where appropriate, aggregates of the particles here is preferably less than the mean diameter $d_{50}$ of the droplets without the finely divided particles.

The mean particle size of the particulate solid (F) is less than 1000 nm, preferably between 10 nm and 800 nm, more preferably between 50 nm and 500 nm, and very preferably between 75 nm and 300 nm, measured in each case as the mean hydrodynamic equivalent diameter by means of photon correlation spectroscopy in 173° backscatter with a Nanosizer ZS from Malvern. The methanol number of the particulate solid (F) is preferably less than 70, more preferably less than 50, very preferably less than 40, and especially preferably less than 30.

The methanol number is determined by preparing defined mixtures of water with methanol, and then determining the surface tensions of these mixtures using known techniques. In a separate experiment, these water-methanol mixtures are overlayered with defined amounts of particles, and shaken under defined conditions (for example, gentle shaking by hand or with a tumble mixer for around 1 minute). A determination is made of the water-alcohol mixture for which the particles just do not sink, and of the water-alcohol mixture of higher alcohol content for which the particles do just sink.

The surface tension of the latter alcohol-water mixture yields the critical surface energy $\gamma_{crit}$ as a measure of the surface energy $\gamma$ of the particles. The methanol content in water gives the methanol number.

The carbon content of the particulate solid (F) is greater than 0 wt %, preferably 0.1-4 wt %, more preferably 0.25-3.5 wt %, and very preferably 0.5-3 wt %, measured by means of elemental analysis on the dry particulate solids.

Further to at least one siloxane or silane, the droplets may additionally comprise further constituents selected for example from catalysts, fillers, inhibitors, heat stabilizers, solvents, plasticizers, color pigments, sensitizers, photo initiators, adhesion promoters, thixotropic agents, conductivity additives, cosmetic substances, fragrances, active medicinal or cosmetic ingredients, and silicone resins.

The particle-stabilized Pickering emulsions (E) of the invention are preferably substantially free from conventional liquid and solid, organic surface-active substances which are nonparticulate at room temperature and under the pressure of the surrounding atmosphere, such as nonionic, cationic and anionic emulsifiers ("organic emulsifiers").

"Organic emulsifiers" here refers not to particles and colloids, but instead to molecules and polymers, in line with the definition of molecules, polymers, colloids and particles as given in Dispersionen und Emulsionen [Dispersions and Emulsions], G. Lagaly, O. Schulz, R. Zindel, Steinkopff, Darmstadt 1997, ISBN 3-7985-1087-3, pp. 1-4.

In general these organic emulsifiers have a size of less than 1 nm, a molar mass<10 000 g/mol, a carbon content >50 wt %, determinable by elemental analysis, and a Mohs' hardness of less than 1.

At the same time the organic emulsifiers from which the emulsions of the invention are substantially free usually have a solubility in water at 20° C. and under the pressure of the surrounding atmosphere, in other words 1013 hPa, homogeneously or in micelle form, of greater than 1 wt %.

The emulsions (E) of the invention may include such organic emulsifiers up to a maximum concentration of less than 0.1 times, preferably less than 0.01 times, more preferably less than 0.001 times, more particularly less than 0.0001 times, the critical micelle concentration of these organic emulsifiers in the water phase; this corresponds to a concentration of these organic emulsifiers, based on the total weight of the dispersion of the invention, of less than 10 wt %, preferably less than 2 wt %, more preferably less than 1 wt %, more particularly 0 wt %.

The mixing with material (S) is preferably preceded by preparation of a preliminary dispersion (V) of the particulate solid (F) in aqueous phase (W).

The preliminary dispersion (V) may be prepared in principle in accordance with the known processes for producing particle dispersions, such as incorporation by means of stirring elements with a high shearing effect, such as high-speed stirrers, high-speed dissolvers, rotor-stator systems, ultrasonic dispersers, or ballmills or beadmills.

The concentration of the solid (F) in the preliminary dispersion (V) in this case is between 1 and 80 wt %, preferably between 10 and 60 wt %, more preferably between 10 and 40 wt %, and very preferably between 12 and 30 wt %.

The particle-stabilized Pickering emulsion (E) may be produced using any of the techniques known to the skilled person for producing emulsions. It has nevertheless emerged that especially suitable emulsions may be obtained in accordance with the following methods:

Method 1:

Initial introduction of a highly concentrated preliminary dispersion (V), the volume initially introduced being made such that it comprises the total amount of required finely divided solid (F) and only a partial amount of aqueous phase (W).

Slow metered addition of the total volume of material (S) with continual homogenizing by means, for example, of a high-speed stirrer, high-speed dissolver or rotor-stator system.

Subsequent slow metered addition of the desired residual volume of aqueous phase (W), optionally with continual homogenization by means, for example, of a high-speed stirrer, high-speed dissolver or rotor-stator system.

Method 2:

Initial introduction of the total volume of material (S).

Slow metered addition of a highly concentrated preliminary dispersion (V), with continual homogenization by means, for example, of a high-speed stirrer, high-speed dissolver or rotor-stator system, the volume metered in being made such that it comprises the total amount of required particulate solid (F) and only a partial amount of aqueous phase (W).

Subsequent slow metered addition of the desired residual volume of aqueous phase (W), optionally with continual homogenization by means, for example, of a high-speed stirrer, high-speed dissolver or rotor-stator system.

Method 3:

Initial introduction of the total volume of material (S).

Slow metered addition of a preliminary dispersion (V), with continual homogenization by means, for example, of a high-speed stirrer, high-speed dissolver or rotor-stator system, the volume metered in being made such that it comprises the total amount of required solid (F) and aqueous phase (W).

Method 4:

Initial introduction of the preliminary dispersion (V), the volume initially introduced being made such that it comprises the total amount of required solid (F) and aqueous phase (W).

Slow metered addition of the total volume of material (S) with continual homogenization by means, for example, of a high-speed stirrer, high-speed dissolver, rotor-stator system or by means of capillary emulsifier.

Method 5:

Initial introduction of the total volume of material (S) and of the preliminary dispersion (V), the volume initially introduced being made such that it comprises the total amount of required particulate solid (F) and aqueous phase (W).

Joint homogenization by means, for example, of a high-speed stirrer, high-speed dissolver or rotor-stator system.

Method 6:

Initial introduction of the total volume of material (S) and of a highly concentrated preliminary dispersion (V), the volume initially introduced being made such that it comprises the total amount of solid (F) and aqueous phase (W).

Joint homogenization by means, for example, of a high-speed stirrer, high-speed dissolver or rotor-stator system.

Subsequent slow metered addition of the desired residual volume of aqueous phase (W), optionally with continual homogenization by means, for example, of a high-speed stirrer, high-speed dissolver or rotor-stator system.

Preference is given to methods 1, 4, 5 and 6, with methods 4 and 5 being particularly preferred and method 5 especially preferred.

The homogenizing takes place preferably in at least one method step for at least 30 seconds, preferably at least 1 minute.

In an optional method step, the aqueous, particle-stabilized Pickering emulsion (E) of the invention is diluted with aqueous phase (W), optionally with continual homogenization by means, for example, of a high-speed stirrer, high-speed dissolver or rotor-stator system.

The methods described may be carried out either in a continuous form or in a discontinuous form. The continuous form is preferred.

The temperature during the emulsifying operation is between 0° C. and 80° C., preferably between 10° C. and 50° C., more preferably between 20° C. and 40° C.

The emulsifying operation may be carried out under atmospheric pressure, in other words at 1013 hPa, at elevated pressure, or under reduced pressure. Operation under atmospheric pressure is preferred.

For the emulsion (E), the particulate solid (F), the material (S) and the aqueous phase (W) are mixed preferably in the following proportions:

(F): preferably 2-15 wt %, more preferably 3-13 wt %, very preferably 4-12 wt %

(S): preferably 50-70 wt %, more preferably 53-68 wt %, very preferably 55-65 wt %

(W): preferably 23-45 wt %, more preferably 25-40 wt %, very preferably 27-36 wt %

Q1 is preferably any number from 5 to 22, more preferably from 8 to 18, more particularly from 10 to 16.

Q2 is preferably any number from 55 to 70, more preferably from 60 to 70.

Q3 is preferably any number from 77 to 89, more preferably from 82 to 88, more particularly from 84 to 87.

After the mixing, the emulsion E may be diluted with any desired amount of water.

The mixing in the process is carried out preferably for shorter than 120 h, more preferably between 0 h to 48 h, very preferably 0.1 h to 24 h, and, in one specific embodiment, 0.25 h to 12 h.

In the process it is possible optionally, in addition to the aqueous phase (W), material (S) and solid (F), to add catalysts as stated above which accelerate and complete the crosslinking. This addition may be made before the Pickering emulsion (E) is produced, directly to the material (S) or to the aqueous phase (W), during mixing, or subsequently, to the completed Pickering emulsion.

The amount used of any catalysts added is within the quantitative range typical for catalysts.

The reaction temperature during mixing is between 0° C. and 150° C., preferably between 10° C. and 80° C. and more preferably between 15° C. and 60° C.

The process may optionally be carried out under an inert gas atmosphere such as nitrogen, argon or carbon dioxide. The oxygen fraction in that case is less than 15 vol %, preferably less than 10 vol % and more preferably less than 5 vol %.

The pH of the emulsion (E) is between pH 10 and 1, preferably between pH 9 and 2, more preferably between pH 7 and 2 and, in one specific embodiment, between pH 6 and 2.5.

The emulsion (E) may optionally be admixed with water-soluble organic solvents such as alcohols such as methanol, ethanol or isopropanol or ketones such as acetone or MEK or ethers such as THE or others. They may be added either directly after the end of the production of the emulsion (E), or during the mixing.

The emulsion (E) may optionally be admixed with dispersing assistants, protective colloids or the like. These may be added either directly after the end of the production of the emulsion (E), or during the mixing.

The emulsion (E) preferably comprises less than 5 wt % of dispersing assistants, protective colloids, or the like; the dispersion of the particles of the invention more preferably comprises less than 1 wt % of dispersing assistants, protective colloids, or the like; very preferably the dispersion of the particles of the invention comprises less than 0.1 wt % of dispersing assistants, protective colloids, or the like, and, in one specific embodiment, the emulsion (E) is free from dispersing assistants, protective colloids, or the like.

Organic or inorganic electrolytes may optionally be added to the emulsion (E). They may be added either directly after the end of the production of the Pickering emulsion, during the reaction phase, or after the end of the reaction phase. The ionic strength of the dispersion in this case is between 0.01 mmol/1 and 1 mol/1, preferably between 0.1 mmol/1 and 500 mmol/1, and very preferably between 0.5 mmol/1 and 100 mmol/1.

Thickeners may optionally be added to the emulsion (E). These may be organic or inorganic thickeners which are present in solid or liquid form at room temperature and under the pressure of the surrounding atmosphere, in other words at 1013 hPa. They may be added either directly after the end of the production of the emulsion (E), or during the mixing.

Prior to the emulsification of the emulsion (E), fillers may optionally be added to the constituent (S), in amounts preferably of 0.1 to 200 parts by weight, more preferably 0.5 to 100 parts by weight, based in each case on 100 parts by weight of material (S). The amount of filler used may be varied within wide ranges and is guided in particular by the respective application of the emulsion (E) of the invention.

The fillers and adjuvants may be added before the Pickering emulsion (E) is produced, directly to the material (S) or to the aqueous phase (W), during emulsification, or subsequently, to the completed Pickering emulsion (E).

Examples of fillers are nonreinforcing fillers, such as, for example, fillers having a BET surface area of up to 50 $m^2/g$, such as quartz, diatomaceous earth, calcium silicate, zirconium silicate, zeolites, aluminum oxide, titanium oxide, iron oxide, zinc oxide, barium sulfate, calcium carbonate, gypsum, silicon nitride, silicon carbide, boron nitride, glass powder and plastics powder.

Examples of reinforcing fillers are the fillers stated above for the particulate solid (F) and having a specific BET surface area of 30 to 500 $m^2/g$, and also silicone resins. Examples of silicone resins are MQ, MT, T, MDQ, MDT, MTQ and MDTQ silicon resins, where M is selected from $R_3SiO_{1/2}$ and $HR_2SiO_{1/2}$ and $R^1R_2SiO_{1/2}$ units, D is selected from $R^1RSiO_{1/2}$ and $R_2SiO_{1/2}$ and $HRSiO_{1/2}$ units, T is selected from $RSiO_{3/2}$ and $R^1SiO_{3/2}$ and $HSiO_{3/2}$ units, and Q denotes $SiO_{4/2}$ units, where R independently at each occurrence, identically or differently, is an organic or inorganic radical which is free from aliphatic carbon-carbon multiple bonds, and $R^1$ independently at each occurrence, identically or differently, is a monovalent, substituted or unsubstituted, SiC-bonded hydrocarbon radical having at least one aliphatic carbon-carbon multiple bond.

Radical R preferably comprises a monovalent, SiC-bonded optionally substituted hydrocarbon radical which is free from aliphatic carbon-carbon multiple bonds and has 1 to 18 carbon atoms, and more preferably comprises a monovalent, SiC-bonded hydrocarbon radical which is free from aliphatic carbon-carbon multiple bonds and has 1 to 6 carbon atoms, and more particularly comprises the methyl or phenyl radical. Radical $R^1$ may comprise any desired groups which are amenable to an addition reaction (hydrosilylation) with an SiH-functional compound.

Radical $R^1$ preferably comprises alkenyl and alkynyl groups having 2 to 16 carbon atoms, such as vinyl, allyl, methallyl, 1-propenyl, 5-hexenyl, ethynyl, butadienyl, hexadienyl, cyclopentenyl, cyclopentadienyl, cyclohexenyl, vinylcyclohexylethyl, divinylcyclohexylethyl, norbornenyl, vinylphenyl and styryl radicals, with particular preference being given to the use of vinyl, allyl and hexenyl radicals.

The silicone resins suitable as fillers are solid at 20° C. and 1013 hPa.

The fraction of the droplets of the invention in the emulsion (E), consisting of the sum total of material (S) used and particulate solid (F), is between 0.1 wt % and 99 wt %, preferably between 5 wt % and 90 wt % and more preferably between 10 wt % and 80 wt %.

The completed emulsion (E) may additionally, optionally, be stored with stirring. This may be accomplished by means, for example, of bar stirrers or anchor stirrers.

Another subject of the present invention is a process for producing particles (P) composed of a core (K) comprising polymeric material and of a shell (H) composed of particulate solid (F), wherein, in a second step, the material (S) of the aqueous particle-stabilized Pickering emulsion (E), which is amenable to polyaddition, to polycondensation or to chain polymerization and is selected from siloxane and silane, is subjected to a polyaddition, chain polymerization or condensation.

The second step is preferably to be performed such that the amount of polymerizable material (S) in the aqueous particle-stabilized Pickering emulsion (E) is less than 70 wt %, preferably less than 60 wt %, more preferably less than 50 wt % and especially preferably less than 40 wt %. Before the second step, the particle-stabilized Pickering emulsion (E) is preferably diluted with water or a water-soluble organic solvent, more preferably with water.

In a process suitable for producing the particles (P), the polymerizable material (S), after the mixing in the first step, is subjected to a polyaddition, chain-polymerized or condensed.

The siloxanes or silanes may need to be hydrolyzed before the condensation, if, for example, they are alkoxy- or acetoxy-substituted silanes or siloxanes. In the case of sufficiently reactive silanes and siloxanes, the water present is enough to bring about, optionally, hydrolysis and subsequently the condensation. In the case of less reactive silanes and siloxanes, catalysts are needed, which bring about, optionally, the hydrolysis and the condensation of the siloxanes and silanes. These catalysts may be acids or bases or else may be metal catalysts, such as group IV transition metal catalysts or tin catalysts, of the kind typically used to accelerate hydrolyses, condensation reactions or transesterification reactions. Suitable acids or bases, in addition to the known mineral acids and metal salts, include acidic or basic silanes or siloxanes.

Preferred basic catalysts are NaOH, KOH, ammonia and $NEt_3$.

Preferred acidic catalysts are p-toluene sulfonic acid, aqueous or gaseous HCl, sulfuric acid.

If the process comprises a chain polymerization reaction, this may be, for example, a radical polymerization reaction of an olefinically unsaturated siloxane or silane.

If the material (S) comprises a silane or siloxane amenable to polyaddition, the material (S) is preferably admixed with transition metal catalysts such as platinum catalysts, for example, especially when it comprises siloxanes able to react with one another in a hydrosilylation reaction.

The process is to be performed such that the finely divided particulate solid (F) stabilizing the siloxane phase or silane phase, during the condensation reaction, the chain polymerization reaction or the polyaddition reaction, reacts with the surface of the condensation or polymerization products forming the cores (K), or at least enters into a stable interaction therewith, such as hydrogen bonds, van der Waals interactions or another directed interaction, or makes a combination of such directed interactions, so that the solid (F) is anchored on the cores (K) composed of the condensation products or chain polymerization products of the material (S).

The surface of the particles (P) may optionally be modified by treatment with reactive silanes or siloxanes. These may be added either directly or after the end of the production of the Pickering emulsion, during the reaction phase, or after the end of the reaction phase, in the second step, before the isolation of the particles (P) or after the isolation of the particles, in liquid or solid phase. This treatment is to be carried out such that there is covalent chemical attachment of the silane or siloxane to the particles. Corresponding methods and processes are known to the skilled person.

The Pickering emulsion (E), after the end of the reaction phase in the second step, may additionally, optionally, be stored with stirring. This may be accomplished for example by means of bar stirrers or anchor stirrers.

In one preferred embodiment the particles (P) are isolated, preferably by sedimentation, filtering or centrifuging, more preferably by filtration or centrifuging, very preferably by centrifugation.

Following isolation, the particles (P) are preferably washed with a washing liquid, which is preferably selected from FD water, methanol, ethanol and mixtures thereof.

In one preferred embodiment the particles (P) are isolated in powder form from the aqueous phase (W). This may be accomplished, for example, by means of filtration, sedimentation, centrifuging, or by removal of the volatile constituents by drying in ovens or dryers, or by spray drying, or by application of an appropriate reduced pressure.

Through spray drying it is possible to obtain a very high fineness of the particles (P) without further working. Particles (P) dried statically tend to form loose agglomerates, which can be deagglomerated by suitable milling processes, such as by ballmill or air-jet mill, for example.

The particles (P) are characterized more particularly in that they have a mean particle diameter $d_{50}$ of 0.5 to 9 μm, preferably of 0.8 to 8.5 μm, more preferably 1.0 to 8.0 μm, very preferably of 1.5 to 7 μm and especially preferably of 2 to 6 μm, measured with a Camsizer X2 from Retsch Technology (measurement principle: Dynamic image analysis according to ISO 13322-2, measuring range: 0.8 μm-30 mm, type of analysis: dry measurement of powders and granules, dispersing pressure=2 bar).

The particles (P) preferably have a narrow particle size distribution range, which is characterized in that the distribution range ($d_{90}$-$d_{10}$) is less than 20 μm, preferably less than 17 μm, more preferably less than 15 μm, and especially preferably less than 8 μm.

The particles (P) are characterized more particularly in that the particulate solids (F) used are bonded substantially on the surface of the polymer particles (P). The distribution of the particulate solids (F) used may be obtained from TEM micrographs of polished thin sections of embedded particles of the invention. The particulate solid (F) is immersed preferably more than 10 nm, more preferably more than 20 nm, very preferably more than 30 nm into the crosslinked polymerization product, and protrudes preferably more than 10 nm, more preferably more than 20 nm, very preferably more than 30 nm from the crosslinked polymerization product, in each case measured from the outer boundary of the crosslinked polymerization product, and so is firmly bonded on the surface of the particle (P). This is a substantial advantage over a commercially available product wherein the completed silicone elastomer particle is after-treated with a silica. In the case of such a product, the silica is not immersed into the silicone elastomer and hence is not firmly bonded on the surface.

The particles (P) are substantially spherical. With preference the sphericity SPHT3 is at least 0.8, more preferably at least 0.82, as determinable according to ISO 9276-6 using a Camsizer X2 from Retsch Technology.

By comparison with noninventive silica-coated particles according to the prior art produced using the same amount of particulate solid (F), the particles (P) have a significantly lower particle size. As a result these particles can be used for applications for which comparatively large silica-coated particles according to the prior art are not suitable. The inventive particles are able, on processing or during application, for example, to pass through significantly smaller openings, gaps or nozzles and hence enable the production of significantly finer structures or surface coatings than is possible with the comparatively large silica-coated particles according to the prior art.

The particles (P) of the invention are amphiphilic, meaning that they are both hydrophilic (i.e., water-loving) and lipophilic (i.e., fat-loving). This means that the particles of the invention are readily dispersible not only in polar solvents, such as water or alcohols, for example, but also in apolar solvents, such as, for example, aliphatic hydrocarbons, or polydimethylsiloxane oils, without the addition of further dispersing assistants or additives, such as organic emulsifiers or other surface-active substances, for example. This is a substantial advantage of the particles (P) of the invention in comparison to uncoated silicone elastomer particles, which are very hydrophobic and which are not dispersible in polar solvents, such as water or alcohols, for example, without the use of unwanted auxiliaries, such as organic emulsifiers. In the case of the particles (P) of the invention, the particulate solid (F) is firmly bonded on the surface, and consequently the amphiphilic properties are retained on dispersion in a solvent. This is a substantial advantage relative to silicone elastomer particles according to the prior art, which after curing are after-treated with silica, since in the case of such particles, not in accordance with the invention, the absorbed silica is not permanently bonded. A disadvantage of these particles according to the prior art is that non-permanently bonded silica is detached wholly or partly when the particles are dispersed in a solvent, so causing the particles to become highly hydrophobic and making them no longer dispersible in polar solvents, such as water, for example.

Another subject of the present invention are addition-crosslinked, condensation-crosslinked or chain polymerization-crosslinked silicone resin particles (P1) having a mean diameter d50 of at most 9 μm, producible by the process described above. Especially preferred are condensation-crosslinked silicone resin particles (P1).

In this case the material (S) amenable to polyaddition, to polycondensation or to chain polymerization is crosslinked to form a thermoset silicone resin.

Preferred examples of silicone resins suitable for the silicone resin particles (P1) are the silicone resins stated above in connection with the reinforcing fillers, these resins being condensation-crosslinked, more particularly the pure T resins.

The aqueous, particle-stabilized Pickering emulsion (E) may be employed for all purposes for which aqueous dispersions are also used to date. The aqueous, particle-stabilized Pickering emulsion (E) may be used for cosmetic and pharmaceutical applications, cleaning and cleansing compositions, or applications involving a change in the interface properties of solid and liquid substrates, such as, for example, hydrophobizing compositions, adhesion promoters, release agents, paper coatings or foam control compositions, for producing w/o/w or o/w/o multiple emulsions, as controlled release systems, for example, or for the segregation of reactive substances.

The Pickering emulsion (E) crosslinks after removal of water and cures to form elastomers or resins. Accordingly the aqueous, particle-stabilized Pickering emulsion (E) may serve, for example, as a sealant and adhesive, paint, coating system, and as an electrically insulating or conducting, hydrophobic coating system repelling sticky substances, or as a base for or addition to such systems. Also possible is the production of shaped articles by crosslinking the emulsion (E).

The Pickering emulsion (E) and the particles (P) are used more particularly in cosmetic products.

The particles (P) exhibit very advantageous behavior, especially for cosmetic applications. They have no propensity toward agglomeration or blocking, and are therefore exceptionally easy to disperse and produce a velvety skinfeel. This behavior is not observed with uncoated silicone elastomer particles not in accordance with the invention. Such particles form a ball when spread on the skin and produce an adverse feel.

In comparison to noninventive particles not coated with silica, the particles (P) have a relatively large surface area. As a result the particles (P) are able to absorb a greater amount of skin fluids and result in a dry skinfeel over a relatively long time.

In comparison to noninventive particles not coated with silica, silica-coated particles are able to absorb a greater amount of functional substances on the silica surface, examples being fragrances, care agents, vitamins or UV absorbers, or active medical ingredients. These substances may then be released on the skin.

In comparison to noninventive particles not coated with silica, the silica-coated particles exhibit amphiphilic behavior, meaning that they are readily dispersible both in oily and in aqueous liquids.

In comparison to noninventive particles not coated with silica, the surface of the silica-coated particles can be wetted more effectively by liquids. As a result the particles can be dispersed substantially more easily and quickly into liquids, such as cosmetic formulations, for example, and they also absorb liquids on the surface much more quickly and easily—for example, they absorb sebum when applied cosmetically on the skin.

In comparison to noninventive silica-coated particles according to the prior art, the particles (P) have a substantially lower particle size. As a result, when spread on the skin in cosmetic applications, they possess a more pleasant and softer skinfeel and produce a more uniform skin appearance as a result of the finer covering of the skin. Unevennesses and marks on the skin are concealed more effectively as a result.

The particles (P) possess a greater surface area in comparison to noninventive, silica-coated particles according to the prior art, and as a result are able to take up larger amounts of skin fluids or functional substances or active medical ingredients.

EXAMPLES

Solids Content:

10 g of aqueous dispersion are admixed with the same amount of ethanol in a porcelain dish and evaporated to constant weight in an $N_2$-purged drying cabinet at 150° C. The mass $m_s$ of the dry residue gives the solids content, according to solids content /%=$m_s$*100/10 g.

Mean Particle Diameter ($d_{50}$):

The $d_{50}$ was determined using a CamsizerX2 from Retsch Technology (measurement principle: Dynamic image analysis according to ISO 13322-2, measurement range: 0.8 μm-30 mm, type of analysis: dry measurement of powders and granules, dispersing pressure=2 bar).

Methanol Number:

The methanol number is determined by preparing defined mixtures of water with methanol. In a separate experiment, these water-methanol mixtures are overlayered with defined amounts of dried particles, and shaken under defined conditions (for example, gentle shaking by hand or with a tumble mixer for around 1 minute). A determination is made of the water-alcohol mixture for which the particles just do not sink, and of the water-alcohol mixture of higher alcohol content for which the particles do just sink. The latter methanol content in water gives the methanol number.

Example 1: Production of an Aqueous Silica Dispersion 1300 g of a partially hydrophobic pyrogenic silica having a residual silanol content of 71% and a carbon content of 0.95%, obtained by reacting a hydrophilic starting silica having a specific BET surface area of 200 m²/g (available under the name HDK® N20 from Wacker-Chemie GmbH, Munich) with dimethyldichlorosilane according to EP 1433749 A1, are incorporated in portions with stirring into 5200 g of fully demineralized (FD) water on a dissolver at 650 rpm. Following complete addition of the silica, dispersing is continued for a further 60 min at 650 rpm. This gives a high-viscosity dispersion with a solids content of 20% and a pH of 4.2.

Example 2: General Procedure for Producing a Pickering Emulsion of Silanes and/or Siloxanes Amenable to Chain Polymerization, to Polycondensation or to Polyaddition, Using an Ultra-Turrax in a Batch Process Step 1: The silica dispersion described in example 1 is weighed out into a suitable 1000 mL stainless steel vessel and agitated with an Ultra-Turrax T50 at 10 000 rpm for 10 min. The viscosity of the dispersion goes down. Optionally FD water is added and mixed homogeneously. The mixed silicone oil component produced according to one of examples 7, 8 or 9 is added to the agitated silica dispersion and then homogenized using the Ultra-Turrax for 10 min at 10 000 rpm with ice cooling. During this procedure the temperature of the mixture ought not to rise above 35° C. The result is a white composition of high viscosity (emulsion (E)).

Step 2: The high-viscosity composition of step 1 is diluted to 30% silicone oil content by addition of three equal-sized portions of FD water. After each portion of FD water, stirring is carried out for 3 minutes at 6000 rpm. This gives a highly mobile, white O/W emulsion.

Example 3: General Procedure for Producing a Pickering Emulsion of Silanes and/or Siloxanes Amenable to Chain Polymerization, to Polycondensation or to Polyaddition, Using a Dissolver Step 1: The silica dispersion described in example 1 is weighed out into a suitable stirring vessel and agitated using a Labo-Top Planetary dissolver from PC Laborsystem, CH, at 6000 rpm for 10 min. In the process, the viscosity of the dispersion goes down. Optionally FD water is added and mixed homogeneously. The mixed silicone oil component prepared according to one of examples 7, 8 or 9 is added to the agitated silica dispersion and homogenized in the dissolver for 10 min at 6000 rpm with water cooling. During this procedure the temperature of the mixture ought not to rise above 35° C. The result is a white, high-viscosity composition.

Step 2: The high-viscosity composition from process step 1 is diluted to 30% silicone oil content at 1000 rpm by addition of three equal-sized portions of FD water. After each portion of FD water, stirring is carried out for 3 minutes at 1000 rpm. This gives a highly mobile, white O/W emulsion.

Example 4: General Procedure for Producing a Pickering Emulsion of Silanes and/or Siloxanes Amenable to Chain Polymerization, to Polycondensation or to Polyaddition, Using an Ultra-Turrax in a Metering Process In contrast to example 2, the mixed oil components are metered in slowly over 15 min with accompanying homogenization with an Ultra-Turrax at 10 000 rpm.

Example 5: General Procedure for Producing Silica-Coated Silicone Particles from Pickering Emulsions of Silicone Oil Components Amenable to Polycondensation A Pickering emulsion amenable to polycondensation is produced according to example B2 or example B3 from a silicone oil component amenable to polycondensation, produced according to example B8 or B9. 250 g of this Pickering emulsion amenable to polycondensation are admixed with 1.5 g of p-toluene-sulfonic acid. The reaction mixture is stirred at room temperature for 24 h. The result is a white, highly mobile dispersion. The particles are removed by filtration and dried in a drying cabinet at 80° C. for 24 h. This gives a fine, white powder.

Example 6: General Procedure for Producing Silica-Coated Silicone Particles from Pickering Emulsions of Silanes and/or Siloxanes Amenable to Polyaddition A Pickering emulsion amenable to polyaddition is produced according to example B2 or example B3 from the silicone oil component B7 amenable to polyaddition. 250 g of this Pickering emulsion amenable to polyaddition are stirred at 80° C. for 24 h. The result is a white, highly mobile dispersion. The particles are removed by filtration and dried in a drying cabinet at 80° C. for 24 h. This gives a fine, white powder.

Example 7: Production of the Silicone Oil Component B7 Amenable to Polyaddition Using a laboratory stirring apparatus, 375 g of a vinyldimethylsiloxy-terminated polydimethylsiloxane having a viscosity of 1 000 mPas (25° C.) and 264 g of a vinyldimethylsiloxy-terminated polydimethylsiloxane having a viscosity of 20 000 mPas (25° C.) were mixed homogeneously. Subsequently 274 g of a vinyl group-containing silicone resin with the compositions $[Me_3SiO_{1/2}]_{26.65}$ $[ViMe_2SiO_{1/2}]_{3.72}$ $[SiO_{4/2}]_{42.78}$ $[HO_{1/2}]_{1.02}$ $[EtO_{1/2}]_{5.93}$ (molecular weight by SEC (toluene eluent): Mw=5300 g/mol; Mn=2560 g/mol) were added and the mixture was stirred until dissolution was complete. Thereafter 0.45 g of a platinum-sym-divinyltetramethyldisiloxane complex-containing solution, which contains 1 wt % of Pt, and 5.6 g of 1,1,3,3-tetramethyl-1,3-divinyldisiloxane were added and combined homogeneously with stirring.

The base composition obtained in this way was mixed homogeneously with 114 g of a copolymer composed of dimethylsiloxy, methylhydrogensiloxy and trimethylsiloxy units, having a viscosity of 40 mPas at 25° C. and an SiH content of 0.40%. The reactive mixture produced is not storable and was emulsified within an hour after production in accordance with example 2 or example 3.

Example 8: Production of the Silicone Oil Component B8 Amenable to Polycondensation The silicone composition B8 amenable to polycondensation that was used was an oligomeric condensation product, containing methoxy groups, of methyltrimethoxysilane having a molecular weight of Mw=1200 and a methoxy group content of around 30 percent by weight, which was produced according to the customary methods.

Example 9: Production of the Silicone Oil Component B8 Amenable to Polycondensation The silicone composition B9 amenable to polycondensation that was used was a silicone resin with the composition $[MeSiO_{3/2}]_{23}$ $[EtO_{1/2}]_{27}$ (molecular weight by SEC (toluene eluent): Mw=2560 g/mol; Mn=900 g/mol; viscosity (dynamic, 25° C.) 25 mPa·s), which was produced according to the customary methods.

TABLE 1a

| | (examples according to the invention) | | | | | |
|---|---|---|---|---|---|---|
| Example | 10 | 11 | 12 | 13 | 14 | 15 |
| Silicone oil component used | B7 | B7 | B8 | B7 | B7 | B7 |
| Viscosity of silicone oil component (mPa*s) | 3500 | 3500 | 30 | 3500 | 3500 | 3500 |
| Crosslinking type* | a | a | c | a | a | a |
| Mixing assembly | Dissolver | Ultra-Turrax | Ultra-Turrax | Dissolver | Ultra-Turrax | Dissolver |
| Rotary speed | 6000 | 10000 | 10 000 | 6000 | 10000 | 6000 |
| Amount of silicone oil component in | 320 | 188 | 188 | 320 | 170 | 319 |

TABLE 1a-continued

| | (examples according to the invention) | | | | | |
|---|---|---|---|---|---|---|
| Example | 10 | 11 | 12 | 13 | 14 | 15 |
| step 1 (g) | | | | | | |
| Amount of silica dispersion from example 1 in step 1 (g) | 190 | 112 | 112 | 240 | 130 | 226 |
| Amount of water in step 1 (g) | — | — | — | — | — | — |
| Production of Pickering emulsion by example | 3 | 2 | 2 | 3 | 2 | 3 |
| Production of particles by example | 6 | 6 | 5 | 6 | 6 | 6 |
| Q1 | 11.9 | 11.9 | 11.9 | 15.3 | 15.3 | 17.0 |
| Q2 | 67.8 | 67.8 | 67.8 | 62.5 | 62.0 | 62.5 |
| Q3 | 86.4 | 86.4 | 86.4 | 86.4 | 85.9 | 89.0 |
| d50/mm | 3.3 | 4.5 | 3.1 | 3.4 | 3.5 | 3.8 |
| Distribution range (d90-d10) | 3.9 | 5.6 | 4.5 | 3.8 | 3.7 | 5.5 |

*Crosslinking type: a = addition-crosslinking;
c = condensation-crosslinking

TABLE 1b

| | (examples according to the invention) | | | | |
|---|---|---|---|---|---|
| Example | 16 | 17 | 18 | 19 | 20 |
| Silicone oil component used | B7 | B7 | B8 | B9 | B8 |
| Viscosity of silicone oil component (mPa*s) | 3500 | 3500 | 30 | 30 | 30 |
| Crosslinking type* | a | a | c | c | c |
| Mixing assembly | Dissol-ver | Dissol-ver | Ultra-Turrax | Ultra-Turrax | Ultra-Turrax |
| Rotary speed | 6000 | 6000 | 10 000 | 10 000 | 10 000 |
| Amount of silicone oil component in step 1 (g) | 320 | 320 | 170 | 170 | 170 |
| Amount of silica dispersion from example 1 in step 1 (g) | 240 | 180 | 130 | 130 | 130 |
| Amount of water in step 1 (g) | 29 | — | — | — | — |
| Production of Pickering emulsion by example | 3 | 3 | 2 | 2 | 4 |
| Production of particles by example | 6 | 6 | 5 | 5 | 5 |
| Q1 | 15.0 | 10.1 | 15.3 | 15.3 | 15.3 |
| Q2 | 59.2 | 68.4 | 62.0 | 62.0 | 62.0 |
| Q3 | 82.6 | 84.2 | 85.9 | 85.9 | 85.9 |
| d50/mm | 7.6 | 6.1 | 2.2 | 3.2 | 2.2 |
| Distribution range (d90-d10) | 15.4 | 8.6 | 4.0 | 3.9 | 3.8 |

*Crosslinking type: a = addition-crosslinking; c = condensation-crosslinking

TABLE 2

| | (examples not according to the invention) | | | | |
|---|---|---|---|---|---|
| Example | C1 | C2 | C3 | C4 | C5 |
| Silicone oil component used | B7 | B7 | B7 | B7 | B8 |
| Viscosity of silicone oil component (mPa*s) | 3500 | 3500 | 3500 | 3500 | 30 |
| Crosslinking type* | a | a | a | a | c |

TABLE 2-continued

| | | (examples not according to the invention) | | | |
|---|---|---|---|---|---|
| Example | C1 | C2 | C3 | C4 | C5 |
| Mixing assembly | Dissolver | Dissolver | Dissolver | Dissolver | Ultra-Turrax |
| Rotary speed | 6000 | 6000 | 6000 | 6000 | 10 000 |
| Amount of silicone oil component in step 1 (g) | 314 | 335 | 297 | 295 | 300 |
| Amount of silica dispersion from example 1 in step 1 (g) | 160 | 210 | 223 | 146 | 100 |
| Amount of water in step 1 (g) | — | 12 | 40 | 49 | — |
| Production of Pickering emulsion by example | 3 | 3 | 3 | 3 | 2 |
| Production of particles by example | — | — | 6 | 6 | 5 |
| Q1 | 11.7 | 15.0 | 12.0 | 7.5 | 6.7 |
| Q2 | 71.8 | 66.1 | 57.6 | 64.0 | 79.0 |
| Q3 | 90.1 | 89.5 | 76.3 | 75.7 | 89.5 |
| $d_{50}$/mm | — | — | 60.0 | 62.5 | 38.1 |
| Distribution range ($d_{90}$-$d_{10}$) | — | — | 129.0 | 110.6 | 66.1 |
| Formation of Pickering emulsion | no | no | yes | yes | yes |

*Crosslinking type: a = addition-crosslinking; c = condensation-crosslinking

Comparative Example C6: Production of a Noninventive Particle According to WO07113095

A silica-coated silicone resin particle not in accordance with the invention was produced according to WO07113095 Example 1a) to 1c). In this case Q1=7.7, Q2=79.5 and Q3=91.5. A solid is obtained having a mean particle size d50=9.3 μm and a distribution range (d90–d10)=27.2.

Use Examples

Example 21: Sensory Evaluation in Cosmetic Application

The sensory quality of the finely divided, silica-coated silicone particles of the invention from examples 13 and 18 and of the noninventive, silica-coated silicone particles from comparative examples C3 and C5 was evaluated by a trained group of subjects. Following application to the skin, the sensory qualities of the residues were evaluated relative to one another. Table 3 shows the average evaluation awarded by the subjects, with the rating 5 corresponding to a preferred velvety-silky skinfeel and the rating 0 to an unwanted scratchy-rough skinfeel.

TABLE 3

| EVALUATION OF SENSORY QUALITIES: | |
|---|---|
| Organopolysiloxane gel | Rating (scale 0 to 5; 5 = optimal evaluation) |
| Example 13 | 1 |
| Example 18 | 2 |
| Comparative example C3* | 3 |
| Comparative example C5* | 4 |

*not according to the invention

Example 22: Use in Coatings

A silicone coating was produced. This was done by homogeneously mixing 2 parts of the finely divided, silica-coated silicone particles of the invention from example 18 with 98 parts of the silicone composition B7, by stirring for 10 min with a dissolver at 6000 rpm, the temperature being held at 20° C. The resulting composition was applied using a 10 μm doctor blade to a glass plate. This gives a smooth, transparent coating.

Comparative Example C7: Use in Coatings

In contrast to example 22, the noninventive, silica-coated silicone particles from comparative example C5 were used. The resulting coating is inhomogeneous and has numerous white grains and streaks.

Example 23: Visual Evaluation in Cosmetic Use 100 mg of the finely divided, silica-coated silicone particles of the invention from example 13 were spread uniformly over a circular area having a diameter of 4 cm on the uncleaned lower arm of a subject. The result is a slightly whitish area of skin, which is dry, uniform and visually homogeneous. This is a sign that sebum present is completely adsorbed by the skin surface.

Comparative Example C8: Visual Evaluation in Cosmetic Use

In contrast to example 23, prior-art silicone particles (Tospearl 2000B microbeads available from Momentive Performance Materials) were used. When being spread, the particles cake together and produce an unattractive, inhomogeneous skin appearance. This is a sign that sebum present cannot be fully adsorbed by the skin surface.

The invention claimed is:

1. A process for producing an aqueous, particle-stabilized Pickering emulsion (E) of a material (S) amenable to polyaddition, to polycondensation or to chain polymerization and selected from siloxane and silane, comprising:
   mixing an aqueous phase (W), a material (S) amenable to polyaddition, to polycondensation or to chain polymerization and selected from siloxane and silane, and a
particulate silicon (IV) oxide solid (F);

forming droplets having a mean diameter d50 of at most
9 μm and comprising the material (S) and the particulate solid (F);

wherein the particle-stabilized Pickering emulsion has a
mass ratio Q1=m(F)/m(S)*100 is any number from 8 to
18, a mass ratio Q2=m(S)/(m(S)+m(W))*100 is any
number from 60 to 70, and the relationship between Q1
and Q2 is Q2=-(1.56 *Q1)+Q3, wherein Q3 is a
number between 82 and 88; and wherein the $d_{50}$ is determined using a dynamic image
analysis according to ISO 13322-2, a measurement
range of 0.8 μm-30 mm, and a measurement of powders
and granules, dispersing pressure=2 bar.

2. The process of claim 1, wherein the material (S) is at
least one siloxane amenable to polyaddition, to polycondensation or to chain polymerization and of the general formula
(IV)

$$[A^1_mR^9_pSiO_{(4-p-m)/2}] \qquad (IV),$$

wherein $A^1$ is a hydrogen or hydrocarbon radical which
contains up to 30 carbon atoms and may additionally
contain heteroatoms selected from O, S, Si, Cl, F, Br,
P or N atoms, and so $A^1$ may also be a functional
group, which itself is unsubstituted or substituted;

wherein $R^9$ denotes alkoxy or aryloxy radicals having
up to 18 carbon atoms, or hydroxyl radicals or H, or
which independently of $A^1$ may have the definition
thereof;

wherein m and p each denote the values 0, 1, 2 or 3;

wherein the sum of m and p is less than or equal to 4;

or at least one silane amenable to polyaddition, to polycondensation or to chain polymerization and of the
general formula (V), $$(R^{10})_{4-o}\text{-Si}\text{—}(OR^{11})_o \qquad (V),$$

wherein o is a number with a value of 1, 2, 3 or 4;

wherein $R^{10}$ denotes linear or branched alkyl radicals
having 1 to 16 carbon atoms, where nonadjacent
carbon atoms may be replaced by oxygen atoms, or
denotes aryl radicals or is an organofunctional radical selected from the group of phosphonic monoester
radical, phosphonic diester radical, phosphonic acid
radical, methacryloyloxy radical, acryloyloxy radical, vinyl radical, mercapto radical, isocyanato radical, where the isocyanato radical may optionally be
reaction-blocked for protection from chemical reactions, hydroxyl radical, hydroxyalkyl radical, vinyl
radical, epoxy radical, glycidyloxy radical, morpholino radical, piperazino radical, a primary, secondary or tertiary amino radical having one or more
nitrogen atoms, where the nitrogen atoms may be
substituted by hydrogen or by monovalent aromatic,
aliphatic or cycloaliphatic hydrocarbon radicals, carboxylic acid radical, carboxylate anhydride radical,
aldehyde radical, urethane radical, urea radical,
where the radical $R^{10}$ may be bonded directly on the
silicon atom or may be separated therefrom by a
carbon chain of 1-6 carbon atoms; and wherein $R^{11}$ is a monovalent, linear or branched aliphatic or cycloaliphatic hydrocarbon radical in
which nonadjacent carbon atoms may be replaced by
heteroatoms such as O, N, P, S, Cl, F, Br or Si, where the free valences of the relevant heteroatoms may be
satisfied by linear or branched alkyl radicals or by
hydrogen atoms, or is a monovalent, aromatic hydrocarbon radical or a radical of the form —C(=O)—
$R^{12}$, where $R^{12}$ is a monovalent, linear or branched
aliphatic or a cycloaliphatic hydrocarbon radical or a
monovalent, aromatic hydrocarbon radical, where
the selected silane or optionally the selected silanes
may be present in nonhydrolyzed form, in hydrolyzed form, or in hydrolyzed and partly condensed or
hydrolyzed and condensed form, or in a mixture of
these forms;

or a preparation of two or more such siloxanes of the
general formula (IV) and/or silanes of the general
formula (V).

3. The process of claim 1, wherein the particulate solid (F)
has a solubility in water at pH 7.33 and an electrolyte
background of 0.11 mol, a temperature of 37° C. and at 1013
hPa of less than 0.1 g/l.

4. The process of claim 1, wherein the mean particle size
of the particulate solid (F) is less than 1000 nm.

5. The process of claim 1, wherein the carbon content of
the particulate solid (F) is 0.1-4 wt %, measured by means
of elemental analysis on the dry particulate solids.

6. A process for producing particles (P) comprising a core
(K) containing polymeric material and a shell (H) composed
of particulate solid (F), comprising:

in a first step, an aqueous, particle-stabilized Pickering
emulsion (E) of a material (S) amenable to polyaddition, to polycondensation or to chain polymerization
and selected from siloxane and silane is produced by
mixing an aqueous phase (W), a material (S) amenable
to polyaddition, to polycondensation or to chain
polymerization and selected from siloxane and
silane, and a particulate silicon (IV) oxide solid (F);

forming droplets having a mean diameter d50 of at
most 9 μm and comprising the material (S) and the
particulate solid (F);

wherein the particle-stabilized Pickering emulsion has
a mass ratio Q1=m(F)/m(S)*100 is any number from
8 to 18, a mass ratio Q2=m(S)/(m(S)+m(W))*100 is
any number from 60 to 70, and the relationship
between Q1 and Q2 is Q2=-(1.56 *Q1)+Q3, wherein
Q3 is a number between 82 and 88; and wherein the $d_{50}$ is determined using a dynamic image
analysis according to ISO 13322-2, a measurement
range of 0.8 μm-30 mm, and a dry measurement of
powders and granules, dispersing pressure=2 bar;
and in a second step, the material (S) of the aqueous, particlestabilized Pickering emulsion (E) is subjected to a
polyaddition, chain polymerization or condensation.

7. The process of claim 6, wherein the particles (P) have
a distribution range $(d_{90}-d_{10})$ of less than 20 μm.

8. The process of claim 6, wherein addition-crosslinked,
condensation-crosslinked or chain polymerization-crosslinked silicone resin particles (P1) having a mean diameter
d50 of at most 9 μm are produced.

9. The process of claim 6, wherein Q1 is 10-16 and Q3 is
84-87.

10. The process of claim 1, wherein Q1 is 10-16 and Q3
is 84-87.

* * * * *